US012694527B2

(12) United States Patent (10) Patent No.: US 12,694,527 B2
Alsheimer et al. (45) Date of Patent: Jul. 28, 2026

(54) METHOD AND IMAGING SYSTEM FOR MATCHING IMAGES OF DISCRETE ENTITIES

(71) Applicant: LEICA MICROSYSTEMS CMS GMBH, Wetzlar (DE)

(72) Inventors: Soeren Alsheimer, Wetzlar (DE); Kai Walter, Wetzlar (DE); Joachim Bradl, Wetzlar (DE)

(73) Assignee: LEICA MICROSYSTEMS CMS GMBH, Wetzlar (DE)

( * ) Notice: Subject to any disclaimer, the term of this patent is extended or adjusted under 35 U.S.C. 154(b) by 575 days.

(21) Appl. No.: 18/152,208

(22) Filed: Jan. 10, 2023

(65) Prior Publication Data

US 2023/0222660 A1 Jul. 13, 2023

(30) Foreign Application Priority Data

Jan. 11, 2022 (EP) .................................... 22150908

(51) Int. Cl.
*G06T 7/00* (2017.01)
*C12Q 1/6818* (2018.01)
(Continued)

(52) U.S. Cl.
CPC .......... *G06T 7/0014* (2013.01); *C12Q 1/6818* (2013.01); *G01N 33/5094* (2013.01);
(Continued)

(58) Field of Classification Search
CPC ............... G06T 7/0014; G06T 2200/04; G06T 2207/10056; G06T 2207/30024;
(Continued)

(56) References Cited

U.S. PATENT DOCUMENTS

2014/0155277 A1* 6/2014 Wiley .................. C12Q 1/6874
506/2
2015/0005176 A1* 1/2015 Kim ........................ G16B 20/10
702/19
(Continued)

FOREIGN PATENT DOCUMENTS

WO PCT/EP2021/058785 4/2021
WO WO 2022/207125 A1 10/2022

OTHER PUBLICATIONS

Gungun Lin et al.: "The Quest for Optical Multiplexing in Bio-discoveries", XP055731604, Chem 4, pp. 997-1021, May 10, 2018, Elsevier Inc., Netherlands.

(Continued)

*Primary Examiner* — Jennifer Mehmood
*Assistant Examiner* — Heath E. Wells
(74) *Attorney, Agent, or Firm* — LEYDIG, VOIT & MAYER, LTD.

(57) ABSTRACT

A method for matching a three-dimensional first image of at least one discrete entity with a three-dimensional second image of the at least one discrete entity is provided. The at least one discrete entity includes a biological sample and a plurality of constituent parts of a marker. The method includes: generating a first representation of the marker from the first image; generating a second representation of the marker from the second image; and based upon the representations matching, matching the first image with the second image; or based upon the representations not matching, rejecting the match. Generating the representations includes determining vectors from at least one reference item to at least some of the constituent parts of the marker, determining for the vectors at least one value of a property, and generating the representations of the marker based on a frequency of the at least one value of the property.

18 Claims, 6 Drawing Sheets

(51) Int. Cl.

| | | |
|---|---|---|
| *G01N 33/50* | (2006.01) | |
| *G01N 33/542* | (2006.01) | |
| *G02B 21/36* | (2006.01) | |
| *H04N 13/207* | (2018.01) | |

(52) U.S. Cl.
CPC ......... *G01N 33/542* (2013.01); *G02B 21/365* (2013.01); *H04N 13/207* (2018.05); *G01N 2458/10* (2013.01); *G06T 2200/04* (2013.01); *G06T 2207/10056* (2013.01); *G06T 2207/30024* (2013.01); *G06T 2207/30096* (2013.01); *G06T 2207/30204* (2013.01)

(58) Field of Classification Search
CPC . G06T 2207/30096; G06T 2207/30204; G06T 7/0012; G06T 2207/10012; C12Q 1/6818; C12Q 1/6825; C12Q 1/6816; G01N 33/5094; G01N 33/542; G01N 2458/10; G02B 21/365; H04N 13/207
USPC ........................................ 382/133
See application file for complete search history.

(56) References Cited

U.S. PATENT DOCUMENTS

| | | | | |
|---|---|---|---|---|
| 2015/0302171 | A1* | 10/2015 | Mori ...................... | G16H 50/20 |
| | | | | 382/131 |
| 2016/0153892 | A1* | 6/2016 | Knebel ................ | G02B 21/367 |
| | | | | 359/385 |
| 2019/0250093 | A1* | 8/2019 | Hart ........................ | G01N 15/00 |
| 2020/0043186 | A1* | 2/2020 | Selviah ..................... | G06T 7/33 |
| 2020/0332351 | A1* | 10/2020 | Chang ................... | C12Q 1/6858 |
| 2021/0110599 | A1* | 4/2021 | Fang .......................... | G06T 7/55 |
| 2022/0270712 | A1* | 8/2022 | Grgicak ................ | G16B 20/00 |
| 2023/0101853 | A1* | 3/2023 | Kodandaramaiah ... | C12M 21/08 |
| | | | | 435/395 |
| 2024/0159647 | A1* | 5/2024 | Alsheimer ........... | G06V 10/426 |
| 2024/0327906 | A1* | 10/2024 | Prosen ................. | C12Q 1/6874 |

OTHER PUBLICATIONS

Bustos et al.: "Feature-based similarity search in 3D object databases", XP058123417, ACM Computing Surveys, ACM, New York, NY, US, vol. 37, No. 4, Dec. 1, 2005 (Dec. 1, 2005), pp. 345-387.

Stephan Preibisch et al.: "Software for bead-based registration of selective plane illumination microscopy data", Nature Methods, Jun. 1, 2010 (Jun. 1, 2010), pp. 418-419, vol. 7, No. 6, XP055874310, New York ISSN: 1548-7091, DOI: 10.1038/nmeth.f.304, Retrieved from the Internet: URL:https://www.nature.com/articles/nmeth0610-418.pdf.

* cited by examiner

600

610

620

METHOD AND IMAGING SYSTEM FOR MATCHING IMAGES OF DISCRETE ENTITIES

CROSS-REFERENCE TO PRIOR APPLICATION

This application claims benefit to European Patent Application No. EP 22150908.6, filed on Jan. 11, 2022, which is hereby incorporated by reference herein.

FIELD

The invention relates to a method and imaging system for matching a three-dimensional first image of at least one discrete entity with at least a three-dimensional second image of the at least one discrete entity, the discrete entity comprising a biological sample and a plurality of constituent parts of a marker.

BACKGROUND

Rare cells, like e.g. adult stem cells, circulating tumor cells and reactive immune cells (e.g. T-Cells, B-Cells, or NK-cells reactive to a certain antigen), are of great interest to basic and translational researchers. Reactive immune cells such as B-cell clones for instance that react to a certain pathogen, e.g. a virus, and can produce antibodies against a particular pathogen are of great value to generate urgently needed therapeutic antibodies. Similarly, reactive T-cells are sought after in the context of personalized medicine and the treatment of cancer and other diseases. Once a reactive T-cell is identified and isolated, the genetic sequence encoding the corresponding T-cell receptor displaying affinity against the target antigen can be cloned and used to generate genetically engineered T-cells such as CAR-T cells. Similarly, circulating tumor cells are expected to have great value for diagnosing cancer, predicting outcomes, managing therapies, and for the discovery of new cancer drugs and cell-based therapeutics. Suspensions of cells containing rare cells are typically derived from either a tissue sample by means of dissociation or from a liquid biopsy. The identification, analysis, and isolation of rare cells in these samples, particularly the analysis of these cells on the single cell level (single cell analysis, SCA) is therefore of great value for basic and translational research, diagnostic and therapeutic applications as well as in the context of bioprocessing and development and manufacturing of biologics and cellular therapeutics.

As the ability to identify and differentiate diverse cell types expands, the identification of cell types becomes more granular, i.e. the rare cell populations of interest are smaller and better defined. Thus, in order to find rare cells of interest a high (<100 k), very high (<1M), or ultra-high (>1M) number of cells typically needs to be analyzed.

Recent progress in the fields of cell culture research has led to the advent of 3D cell culture, which is based on cultivating cells in three dimensions, for example, in suspension culture (scaffold-free techniques) or embedded in hydrogels and/or extracellular matrices (scaffold-based techniques). Hydrogels and extracellular matrices have been used extensively in conjunction with other elements for scaffold-based 3D cell culture. Cells and other elements can be efficiently embedded into discrete entities such as hydrogel beads by various means, cultivated in suspension, and imaged. Various forms of hydrogel beads including single-phase, multi-phase, mixed phase, hollow as well as solid core hydrogel beads with or without a shell can be manufactured using a variety of approaches including microfluidics, 3D printing, emulsification or electro-spraying. This allows cultivation of large numbers of cells, including rare cells, for analytical, diagnostic and therapeutic purposes in a 3D cell culture.

The cultivation of cells embedded in hydrogels (i.e. scaffold-based cell culture), which are kept in suspension, combines the benefits of scaffold-based cell culture with the benefits of suspension cell culture and is thus an attractive mode of cell culture for a wide range of applications. For many workflows that could be based on this type of cell culture, it would be required to be able to repeatably recognize individual discrete entities. For example, in case of handling a large number of single cells, including rare cells, in a collective 3D cell culture, it is of great interest to be able to follow individual entities or cells, for example, over the course of an experiment. This would allow identification, analysis, and isolation especially of rare cells within the large number of cells. However, handling large numbers of entities and cells in a single vessel, whilst keeping track of each, is currently not possible.

SUMMARY

In an embodiment, the present disclosure provides a method for matching a three-dimensional first image of at least one discrete entity with at least a three-dimensional second image of the at least one discrete entity. The at least one discrete entity includes a biological sample and a plurality of constituent parts of a marker. The method includes: generating a first representation of the marker from the three-dimensional first image; generating a second representation of the marker from the three-dimensional second image; and based upon the first representation and the second representation matching, matching the three-dimensional first image with the three-dimensional second image; or based upon the first representation and the second representation not matching, rejecting the match. Generating the first representation and the second representation includes determining vectors from at least one reference item to at least some of the plurality of constituent parts of the marker, determining for the vectors at least one value of a property of the vectors, and generating the first representation or the second representation of the marker based on a frequency of the at least one value of the property.

BRIEF DESCRIPTION OF THE DRAWINGS

Subject matter of the present disclosure will be described in even greater detail below based on the exemplary figures. All features described and/or illustrated herein can be used alone or combined in different combinations. The features and advantages of various embodiments will become apparent by reading the following detailed description with reference to the attached drawings, which illustrate the following.

DETAILED DESCRIPTION

Figure 1:
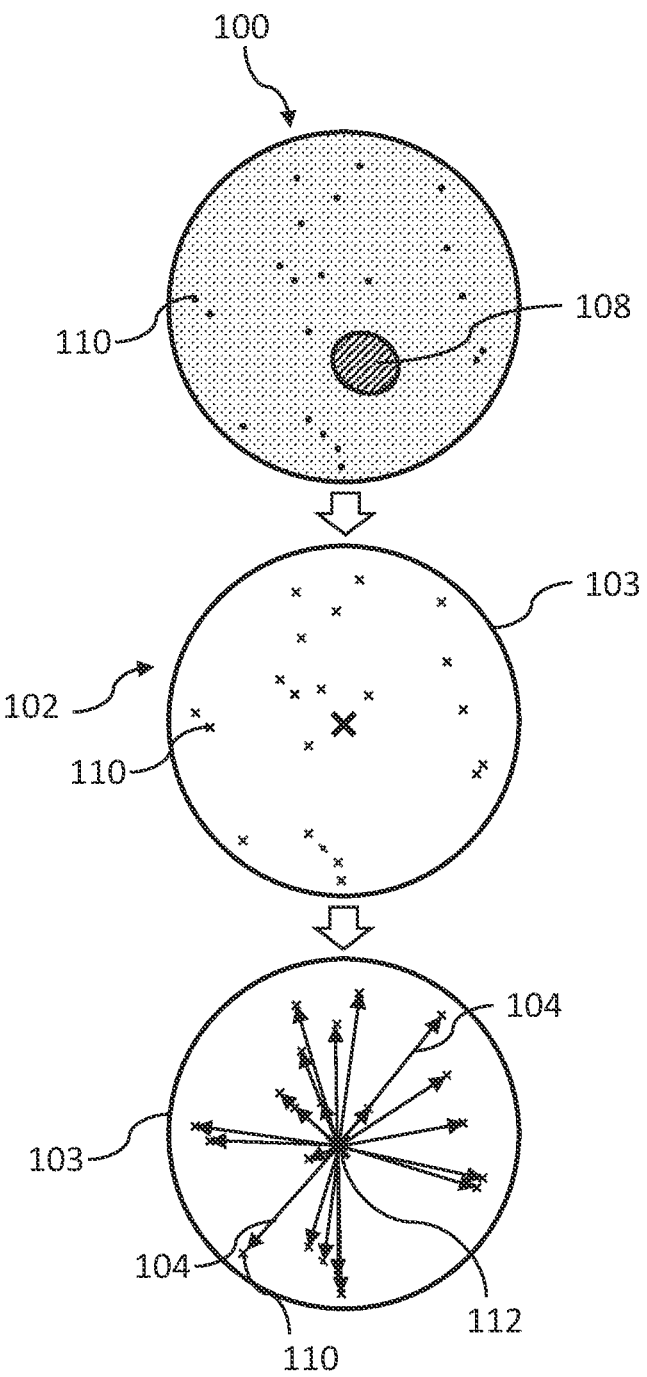
FIG. 1 shows a schematic view of a discrete entity with a marker, a schematic image of the discrete entity with the marker, and the image of the discrete entity with determined vectors.

Embodiments of the present invention provide a method and imaging system that enable keeping track of embedded biological samples in a fast and efficient way.

In an embodiment, a method is provided for matching a three-dimensional first image of at least one discrete entity with at least a three-dimensional second image of the at least one discrete entity, the discrete entity comprising a biological sample and a plurality of constituent parts of a marker, the method comprising the following steps: generating a first representation of the marker from the three-dimensional first image; generating a second representation of the marker from the three-dimensional second image; and matching the three-dimensional first image with the three-dimensional second image, when the first representation and the second representation match, or rejecting the match, when the first representation and the second representation do not match. The steps for generating the representations comprise: determining vectors from at least one reference item to at least some of the constituent parts of the marker, in particular determining vectors from at least one reference item to the center of mass of at least some of the respective constituent parts of the marker, determining for the vectors at least one value of a property of the vectors, and generating the representation of the marker based on the frequency of the values of the property.

The discrete entity can be, for example, a hydrogel bead. The biological sample can comprise, in particular, at least one cell.

The marker of the at least one discrete entity can be, in particular, an optically detectable pattern, structure and/or distribution, that can be read-out by means of a microscope, for example.

The three-dimensional image can be, for example, a z-stack, or image stack, comprising a plurality of two-dimensional images of the discrete entity, in particular, of parallel images. Such a stack of images enables generating the three-dimensional image of the respective discrete entity.

Prior to carrying out the method, feature extraction may be carried out on the image data of the first and second images. Feature extraction is typically performed by feeding n-dimensional image data of the first and second image through a suit-able image processing pipeline or algorithm. Such an image processing pipeline may include background removal, compression, filtering, denoising, enhancement, reconstruction, correction, deconvolution, multi-view deconvolution, multi-view registration, multi-view fusion, and include an image segmentation step, which generates a set of segmented features of the discrete entity, as well as a feature classification step. The result of image segmentation and/or feature classification is typically a segmented virtual discrete entity, its center of mass, the identified constituent parts of the marker as well as features belonging to the biological sample. Feature classification algorithms based on classical approaches, e.g. filtering for size, color, shape, etc., as well as machine or deep learning based approaches may be used to reliably classify features into one of the aforementioned categories, i.e. as belonging to the discrete entity, the marker, or the biological sample.

The representations can thus be generated based on values of properties of the vectors of the respective discrete entity. In particular, the representations can be rotation invariant or angle invariant. This means, that the generated representations of a particular discrete entity are the same irrespective of the angle, at which the discrete entity was imaged at. Thus, the representation does not change with the rotation of the discrete entity.

The reference item may be a feature of the discrete entity, such as the center of mass of the discrete entity, the biological sample, or one of the constituent parts of the marker, in particular, the center of mass of one of the constituent parts of the marker.

The step of matching or rejecting the first image with the second image, in particular, can involve comparing the representations of the first image and the second image and based on their identity and/or similarity matching the first image with the second image or rejecting the match between the first image and the second image.

For an example of a hydrogel bead comprising a marker and for an example of a generalized method for recognizing a hydrogel bead comprising a marker, reference is made to the applications PCT/EP2021/058785 and PCT/EP2021/061754, the content of which is full incorporated herein by reference.

In a preferred embodiment, the property of the vectors is the length of the vectors or the angle between the vectors. In particular, the angles between vectors can be angles between pairs of vectors that intersect. These properties are, in a particularly preferred embodiment, due to them being consistent irrespective of the angle at which the discrete entity with the marker is viewed or of the angle at which the discrete entity with the marker is imaged.

In a particularly preferred embodiment, the representation is generated as a hash value of the frequency of the values of the property. The hash values are particularly efficiently compared to each other. Thus, this enables particularly efficient comparison and/or matching of representations.

In a preferred embodiment, the first image is matched with the second image, when the hash value of the first representation and the hash value of the second representation are identical. This enables particularly fast and efficient matching of images.

In a preferred embodiment, the frequency of the values of the property is determined with a histogram. This enables efficient generation of representations.

In a preferred embodiment, when rejecting the match, when the first representation and the second representation do not match, a similarity score is determined between the first representation and the second representation and the first representation and the second representation are matched in relation to a predetermined level of the similarity score. Thus, when the first and second representations initially do not match, they may be matched based on their degree of similarity rather than their identity. This enables probabilistic matching of representations and thus of images and discrete entities.

In a particularly preferred embodiment, the similarity score is determined based on a Kullback-Leibler divergence.

In a preferred embodiment, when rejecting the match, when the first representation and the second representation do not match, the representations are regenerated from the images by determining vectors from the at least one reference item to more than the at least some of the constituent parts of the marker when generating the representations. This might enable a matching of similar representations.

In a preferred embodiment, the reference item is at least one of: a center of mass of the discrete entity, an optically detectable feature of the discrete entity, or a center of mass of one of the constituent parts of the marker. The reference item need not be a point object, rather it may extend in at least one dimension, and in a preferred embodiment, in two dimensions. Thus, the reference item may be a planar object, for example. Further, the reference item may comprise at least one starting point of the vectors, which may be a center of mass of the reference item, for example.

In a preferred embodiment, the images are acquired by means of a microscope or a macroscope, in particular a light sheet microscope. This enables efficiently generating three-dimensional images of the discrete entity.

In a preferred embodiment, the discrete entity is comprised of a polymeric compound. The polymeric compound can be polymerized to form the discrete entity. In particular, the polymeric compound can form a hydrogel. The diameter of the discrete entities or hydrogel beads may be in the range of 10 μm to 10 mm. Particularly preferred ranges are 10 μm to 100 μm, 50 μm to 250 μm and 500 μm to 5 mm. This enables culturing of the biological sample in the discrete entity in scaffold-based suspension 3D cell culture, which combines the benefits of 3D suspension cell culture and scaffold-based cell culture.

In a preferred embodiment, the constituent parts of the marker are microbeads, at least a partial surface of the discrete entity, which is stained with at least one fluorescent dye, or an area of the discrete entity, which is stained with at least one fluorescent dye. The microbeads are, in particular, fluorescent microbeads. The microbeads may have a diameter in the range of 50 nm to 500 nm. Similar to the reference item, the constituent parts of the marker need not be point objects, rather they may extend in at least one dimension, preferably in two dimensions. Thus, the constituent parts may be planar, spherical, spheroidal or elliptical objects, for example. Further, the constituent parts may each comprise at least one finishing point of the vectors, which may be a center of mass of the particular constituent part, for example.

In a preferred embodiment, the three-dimensional image is acquired by combining multiple, parallel images acquired throughout the discrete entity. The three-dimensional image can be, for example, a z-stack, or image stack, comprising a plurality of two-dimensional images of the discrete entity, in particular, of parallel images. Such a stack of images enables generating the three-dimensional image of the respective discrete entity. This enables determining vectors and associated values of the property of the vectors independent of the angle at which the discrete entity is imaged.

In a preferred embodiment, the biological sample comprises at least one cell. This enables tracking the cell embedded in the discrete entity by repeatedly imaging the discrete entity with the marker and the biological sample and matching the images based on the representations.

In a further aspect, an imaging device is provided for matching a three-dimensional first image of at least one discrete entity with at least a three-dimensional second image of the at least one discrete entity, the discrete entity comprising a biological sample and a plurality of constituent parts of a marker, the device comprising: an imaging container to contain at least the one discrete entity, in particular, the discrete entity is at least partially suspended in a liquid in the container; a detector and optical means for imaging at least partially the discrete entity onto the detector; and a control unit configured to: acquiring the three-dimensional first image of the at least one discrete entity; generating a first representation of the marker from the first image; acquiring the three-dimensional second image of the at least one discrete entity; generating a second representation of the marker from the second image; and matching the first image with the second image, when the first representation and the second representation match, or rejecting the match, when the first representation and the second representation do not match. Generating the representations comprises: determining vectors from at least one reference item to at least some of the constituent parts of the marker; determining for the vectors at least one value of a property of the vectors; and generating the representation of the marker based on the frequency of the values of the property.

The imaging device has the same advantages as the method described above. In particular, the imaging device may be amended by the features of the method.

In another further aspect, a computer-program product is provided comprising a program code which, when executed by a computer, causes the computer to carry out the method for matching a three-dimensional first image of at least one discrete entity with at least a three-dimensional second image of the at least one discrete entity.

In another further aspect, a computer-readable medium comprising a program code which, when executed by a computer, causes the computer to carry out the method for matching a three-dimensional first image of at least one discrete entity with at least a three-dimensional second image of the at least one discrete entity.

In another further aspect, a computation device being adapted to execute a program code which, when executed by the computation device, causes the computation device to carry out the method for matching a three-dimensional first image of at least one discrete entity with at least a three-dimensional second image of the at least one discrete entity.

The imaging device has the same advantages as the method described above. In particular, the imaging device may be supplemented using the features of the method.

Further features and advantages of embodiments of the invention are described with reference to the accompanying drawings.

FIG. 1 shows a schematic view of a discrete entity 100 with a marker 102, a schematic image 103 of the discrete entity 100 with the marker 102 and the image 103 of the discrete entity 100 with determined vectors 104.

The discrete entity 100 is preferably made of a polymeric compound, in particular, a polymeric compound that forms a hydrogel and/or that is substantially transparent. The discrete entity may be referred to as a hydrogel bead 100. The shown hydrogel bead 100 is one example of a plurality of hydrogel beads. The polymeric compound may be of natural or synthetic origin, including for example, agarose, alginate, chitosan, hyaluronan, dextran, collagen and fibrin as well as poly(ethylene glycol), poly(hydroxyethyl methacrylate), poly(vinyl alcohol) and poly(caprolactone). The hydrogel bead 100 may be made of a single or several different polymeric compounds. The several different polymeric compounds may be arranged in sections of the hydrogel bead 100, with the sections having different properties. These properties include physicochemical properties such as Young's modulus, refractive index, and chemical composition and functionalization.

The shape of the hydrogel bead 100 is spherical. Alternatively, the hydrogel bead 100 may have a different shape such as a spheroid. The diameter of the hydrogel bead 100 may be in the range of 10 μm to 10 mm. Particularly preferred ranges are 10 μm to 100 μm, 50 μm to 250 μm and 500 μm to 5 mm.

Further, the hydrogel bead 100 comprises a biological sample 108 such as a single cell, several individual cells, or a cell cluster such as a spheroid. The cells may include eukaryotic or prokaryotic cells, such as archaea, bacteria, plant, mammalian, or fungal cells. For the plurality of hydrogel beads 100, each hydrogel bead 100 may comprise a dedicated biological sample 108.

In addition, the hydrogel bead 100 comprises a plurality of microbeads 110, in particular fluorescent microbeads 110. The microbeads 110 might be included and randomly dispersed in the hydrogel bead 100 during the formation of the hydrogel bead 100. After the formation of the hydrogel bead 100, the microbeads 110 are set in place in the hydrogel bead 100. This means the microbeads 110 do not change their location in the hydrogel bead 100 once the hydrogel bead 100 is formed, resulting in substantially stable discrete entities or hydrogel beads 100. The diameter of the microbeads 110 is in the range of 50 nm to 500 nm.

Each of the microbeads 110 is a constituent part of the marker 102. This means the marker 102 comprises the microbeads 110. Further, the random dispersion of the microbeads 110 during formation of the hydrogel bead 100 results in a random placement of the microbeads 110 in each generated hydrogel bead 100. Since the microbeads 110 are randomly dispersed in three dimensions in the hydrogel bead 100 during its formation, a large number of different markers 102 can be generated for the discrete entities 100. Depending on the number of microbeads 110 in the hydrogel bead 100 and the number of hydrogel beads 100, the random placement results in a unique placement in each hydrogel bead 100. Thus, the placement of the constituent parts of each marker 102 of each hydrogel bead 100 in the plurality of hydrogel beads 100 differs from the placement of each remaining marker 102. Therefore, the marker 102 of each hydrogel bead 100 is unique with respect to this placement. Since the marker 102 of the hydrogel bead 100 is unique, the marker may be used to identify the hydrogel bead 100 or recognize the hydrogel bead 100 repeatedly.

In an alternative example, the constituent parts of the marker 102 may be generated after the formation of the hydrogel bead 100. This can be achieved by including compounds in the hydrogel bead 100 when forming the hydrogel bead 100 that generate the constituent parts of the marker after the formation of the hydrogel bead 100. Compounds can be included in the hydrogel bead 100 that can be activated, deactivated or bleached photochemically after formation of the hydrogel bead 100. In a subsequent lithographic, in particular in a photolithographic step, the compounds may be activated, deactivated or bleached photochemically by means of a focused light beam, or by imaging or projecting a pattern on the hydro-gel bead 100. Further, a multi-photon photolithographic device may be used to generate photochemically or photophysically changed areas that are arranged in a pattern in the hydrogel bead 100. These changed areas may be the constituent parts of the marker 102. When generating the pattern of changed areas, they may be generated such that for each hydrogel bead 100 in the plurality of hydrogel beads, a unique pattern of changed areas is generated.

The constituent parts of the marker 102 may be point objects, for example in the form of the microbeads 110. Alternatively, the constituent parts of the marker 102 may extend in at least one dimension, preferably two dimensions, for example the constituent parts may be dyed areas on the spherical surface of the hydrogel bead 100, or areas generated photolithographically, as described above. Such an area may have a rectangular shape or a triangular shape, for example.

Alternatively, the marker 102 may comprise only a selection of constituent parts, in particular, a selection of the microbeads 110 from the plurality of microbeads 110. The selection of microbeads 110 may, for example, be made by predetermined parameters, for which lower and upper limits may be set, such as, number of microbeads 110, a minimum and/or maximum distance to neighbouring microbeads 110, average brightness, color, life-time of fluorescent microbeads 110.

In any case, the constituent parts of the marker 102 are optically detectable, for example, as a phase or intensity object by means of a microscope. Thus, the marker 102 is optically detectable. The hydrogel bead 100 is required to be transparent, at least to an extent that allows the sample 108 and the marker 102 to be optically detectable.

Thus, when imaging the hydrogel bead 100, the image 103 is generated with the constituent parts 110 of the marker 102. In the image data of the image 103, the features of the hydrogel bead 100, such as its center of mass 112, or the microbeads 110, are identified, for example by image segmentation. In addition, features of the constituent parts constituent parts of the marker 102 may be deter-mined, such as the center of mass of some or all of the constituent parts of the marker 102.

Based on the image 103 and the identified features, vectors 104 may be deter-mined between a reference item of the hydrogel bead 100 and the constituent parts of the marker 102. In FIG. 1, the reference item is the center of mass 112 of the hydrogel bead 100. In the case shown in FIG. 1, both, the reference item and the constituent parts of the marker 102 are point objects. Thus, the vectors 104 are drawn from the center of mass 112 of the hydrogel bead 100 to each of the microbeads 110. Based on the vectors 104, a representation of the marker 102 of the hydrogel bead 100 may be generated.

In an alternative embodiment, the reference item may be a feature of the discrete entity 100, for example, the biological sample 108 or a particular one of the constituent parts of the marker 102.

In another alternative embodiment, the reference item and/or the constituent parts of the marker may not be point objects. In this case a particular feature of the reference item or constituent part may be used as starting or finishing point for a particular vector, for example, the starting or finishing point may be a center of mass, a vertex, such as a corner of a polygon, or the vector may be determined along the shortest distance between the reference item and one of the constituent parts of the marker. As a consequence, the reference item may comprise a plurality of starting points for the vectors. In case the reference item or the constituent parts are planar objects, the vectors may be determined as perpendicular to the plane of the object.

In case it is possible to determine more than one vector between a reference item and a constituent part of the marker, the particular constituent part may be excluded when generating the representation in order to avoid ambiguity.

It is noted, that the depiction in FIG. 1 of the hydrogel bead 100, the image 103 and the image 103 with determined vectors 104 is two-dimensional, for simplification of the depiction. However, as described above, the hydrogel bead 100 is a three-dimensional object. The image 103 is a three-dimensional image, for example, a z-stack, or image stack, comprising a plurality of images of the discrete entity 100, in particular, of parallel images. Such a z-stack enables generating a three-dimensional image or representation of the respective discrete entity 100. The images may be generated by a microscope, in particular, a light-sheet microscope.

Figure 2:
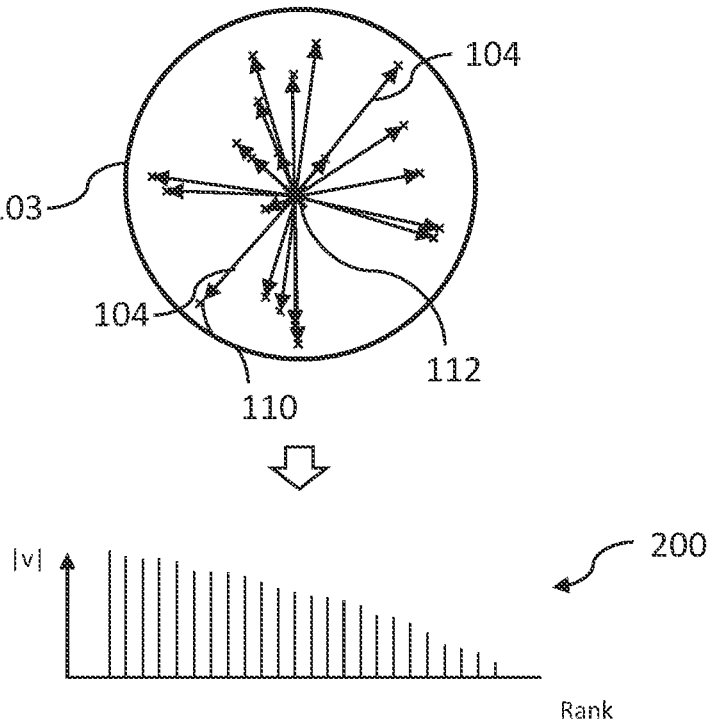
FIG. 2 shows the image of the discrete entity with the determined vectors and a representation of the marker of the discrete entity.

FIG. 2 shows the image 103 of the discrete entity 100 with the determined vectors 104 and a representation 200 of the marker 102 of the discrete entity 100. The representation 200 is a schematic depiction of values of a property of the vectors 104. By way of example, the property may be the length of the determined vectors 104 of the marker 102 of the hydrogel bead 100, depicted in FIG. 2 as the ranked length of all determined vectors 104.

The unique placement of the constituent parts of the marker 102 within the hydrogel bead 100, as described above, leads to the aggregate of the distances be-tween the reference item, here the center of mass 112, and each of the constituent parts to be unique to the hydrogel bead 100. Thus, the uniqueness of the marker 102, as the collection of individual constituent parts, is preserved in the representation 200. This enables the comparison of three-dimensional images of the hydrogel bead 100 based on the representations generated from the three-dimensional images. Rather than comparing the images directly, the representations generated from the images are compared in order to match several images of the hydrogel bead 100 with each other. Thus, when there are three-dimensional images of the hydrogel bead 100 from separate imaging events, representations can be generated for each image, the representations matched and the imaged hydrogel bead 100 recognized as the same.

Moreover, the representation 200 generated based on values of a property of the vectors 104 are rotation invariant or angle invariant. This means, that the generated representations of a particular hydrogel bead 100 are the same irrespective of the angle, at which the hydrogel bead 100 was imaged and based on which three-dimensional image the representation was generated. Thus, the representation does not change with the rotation of the hydrogel bead 100.

Figure 3:
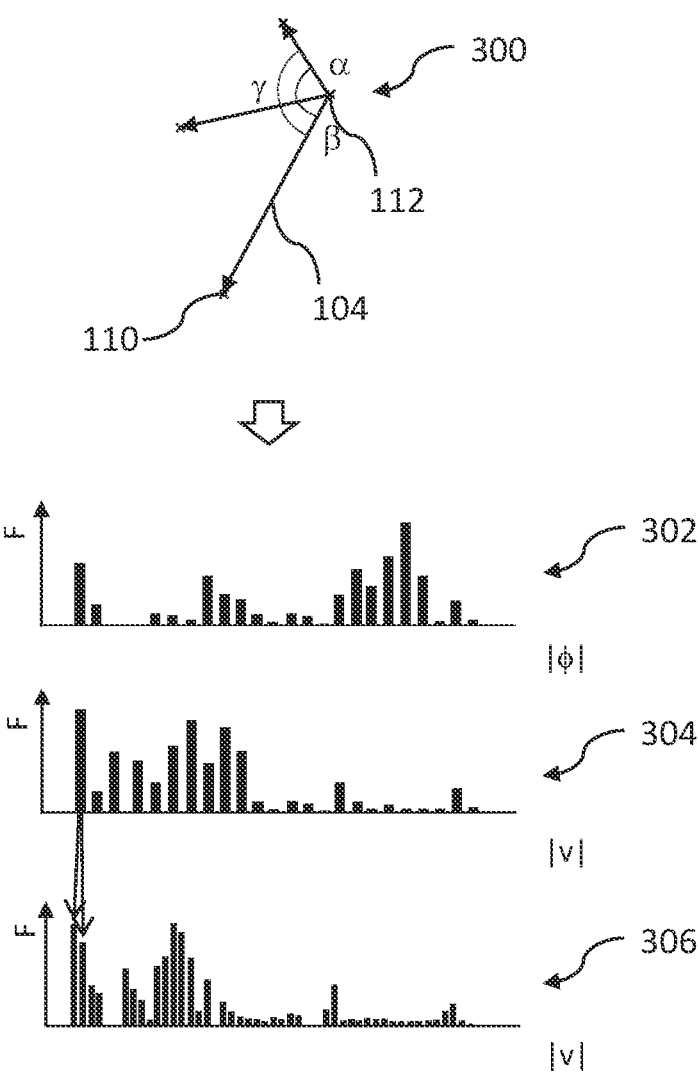
FIG. 3 shows examples of a property of the vectors for generating representations of the marker.

FIG. 3 shows further examples of properties of the vectors 104 for generating representations of the marker 102. Further properties of the vectors 104 may be angles 300 between the vectors 104, in particular, between pairs of vectors 104 that have the same starting point in the reference item and that therefore intersect in the starting point, such as the center of mass 112. The angles 300 in FIG. 3 are denoted by letters $\alpha$, $\beta$ and $\gamma$.

Further, as described above, based on the values of properties of the vectors 104, such as the angles 300 between vectors 104 or length of the vectors 104, a representation may be generated. Alternatively to the representation 200, that is the ranked length of the vectors 104 of the marker 102, a histogram may be generated from the values of one of the properties of the vectors 104. A representation 302 is an example of a representation generated as a histogram based on the angles 300 between vectors 104 for a particular marker. In contrast, a representation 304 is an example of a representation generated as a histogram based on the lengths of the vectors 104 for a particular marker. When comparing and matching representations 200, 302, 304 only representations 200, 302, 304 based on the same property of the vectors 104 should be used.

In addition to using different properties of the vectors 104 when generating representations, the bin size may be varied when using histograms to generate the representations. By way of example, a representation 306 is depicted, which has a smaller bin size compared to the representation 304 and is based on the same values of the length of vectors 104. By using a narrower bin size, the sensitivity of the histogram to variations in the measured values of the properties of the vectors 104 for the same marker 102 increases. In contrast, by using a wider bin size, the robustness of the matching of representations to each other may increase, since small variations in the measured values of the properties of the vectors 104 may not change the histogram.

Figure 4:
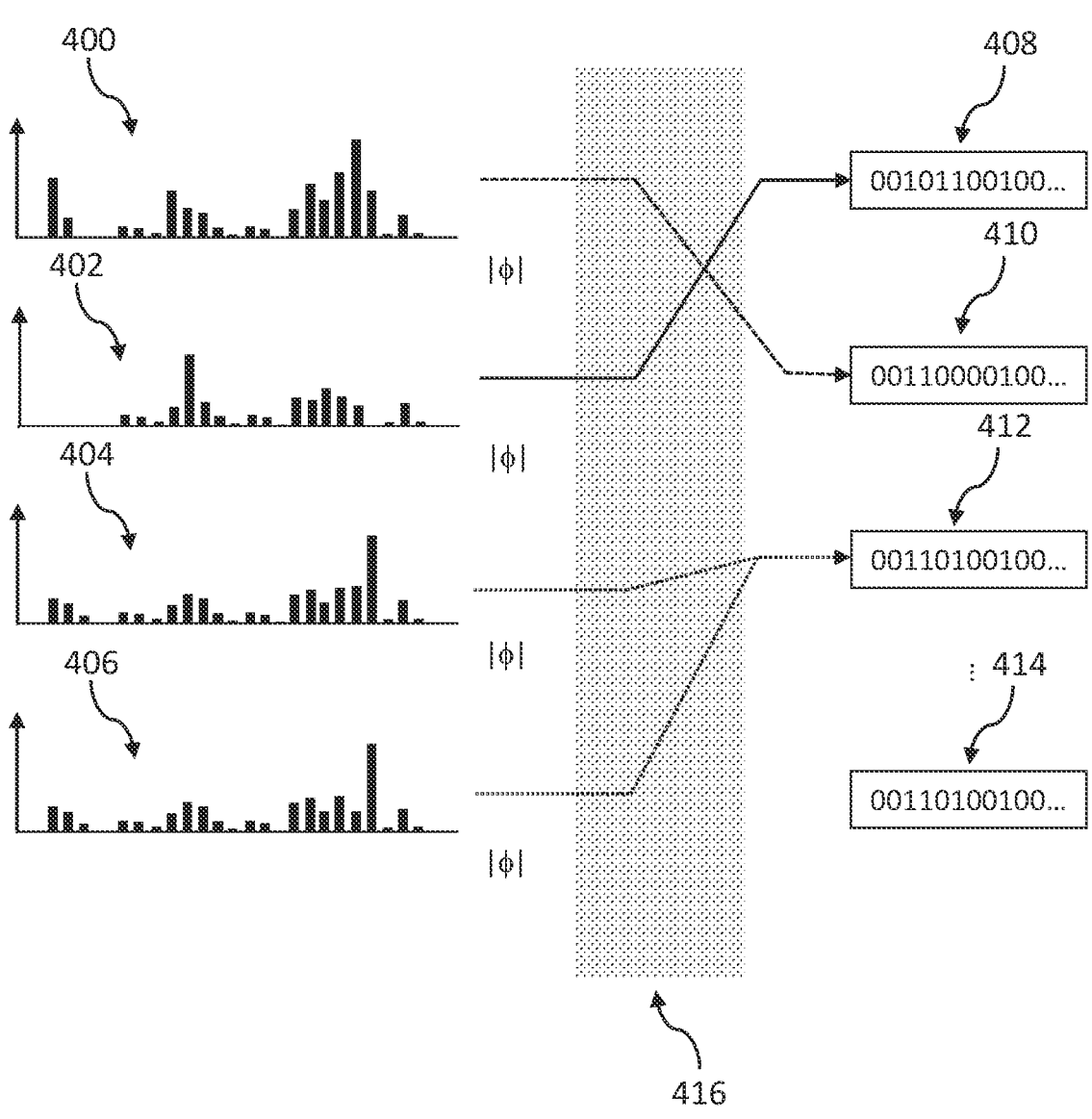
FIG. 4 shows the representation generated as a hash value.

FIG. 4 shows the representation generated as a hash value. Specifically, based on the values of the length of the vectors between reference item and constituent parts of a marker in the histograms 400, 402, 404, 406, corresponding hash values 408, 410, 412, 414 may be generated by a hash function 416. The hash values 408, 410, 412, 414 thus being the representation of a corresponding marker of a hydro-gel bead. The hash values 408, 410, 412, 414 are particularly easy to compare and match to each other.

There is the possibility for the hash function 416 producing the same hash value for only slightly differing histograms. For example, in case of the hash values 412, 414, the actual values are the same, despite the corresponding histograms 404, 406 being slightly different from each other. Thus, when comparing images of a plurality of hydrogel beads 100 from a first round of imaging (each hydrogel bead 100 having a unique marker 102) to images of the plurality of hydrogel beads 100 from a second round of imaging based on the representations, it may be that some of the images from one round may not be matched to the corresponding images from the other round in order to recognize one particular hydrogel bead 100 from one round as the corresponding hydrogel bead 100 from the other round of imaging. In order to resolve this collision, the representations that are used to match the images of corresponding hydrogel beads 100 to each other may be re-generated from a histogram with narrower bin size, as described above. Alternatively, the representations may be matched based on a similarity score in order to compare representations. The similarity score may, for example, be a Kullback-Leibler divergence. In a further alternative, the representations that cannot be matched and the corresponding images and hydrogel beads 100 may be excluded from matching.

Figure 5:
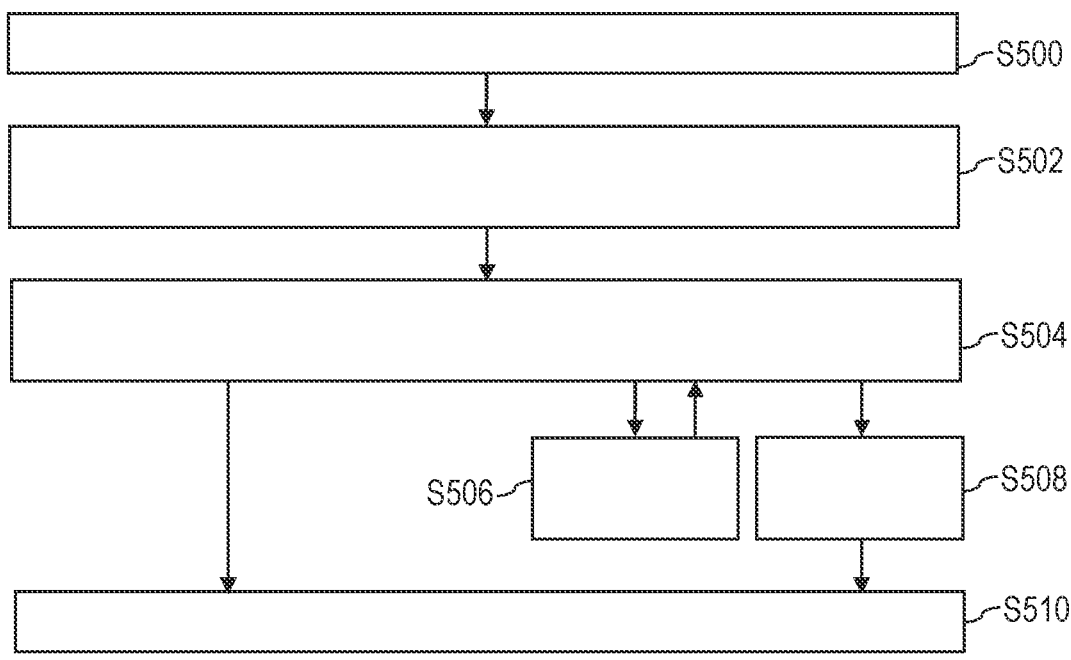
FIG. 5 shows a flow chart of a method for matching a first three-dimensional image of a discrete entity to a second three-dimensional image of the discrete entity.

FIG. 5 shows a flow chart of a method for matching a first three-dimensional image of at least one discrete entity 100 to a second three-dimensional image of the at least one discrete entity 100. The method starts in step S500. In step S502 a representation is generated from each of the three-dimensional first image and the three-dimensional second image of the hydrogel bead 100.

Prior to carrying out the method according to FIG. 5, the first and second image may be analyzed to identify the constituent parts of the marker 102 in each image, for example, by image segmentation. Alternatively, this analysis may be carried out in step S502.

Further, in step S502 vectors 104 are determined for each image between a reference item of the imaged hydrogel bead 100 and at least part of the constituent parts of the marker 102. Subsequently, for the determined vectors 104 values of a property of the vectors 104 is determined. As described above, the property may be lengths of the vectors 104 or angles between vectors. A first representation is then generated from the values of the property of the vectors 104 of the first image and a second representation is then generated from the values of the property of the vectors 104 of the second image. For example, the representation may be a ranked list of the values, a histogram of the values, or a hash value generated based on the values.

In step S504 the representations generated in step S502 are matched to each other when the first and the second representation are matched. This means, that the representations are compared and when the first representation is identical to the second representation, they are matched. In case the representations are matched, the method ends in step S510.

Alternatively, the match is rejected, when the first and second representations do not match, meaning, they are not identical. In this case, the method may initially proceed in step S506. In step S506 the representations may then be regenerated. For example, when a histogram is used, the representations may be regenerated with a narrower bin size. This increases the sensitivity of the representation to variations in the determined values of the properties of the vectors 104 for the same marker 102. Alternatively and in case when the representations were generated the vectors 104 were determined only to a part of the constituent parts of the marker 102, the representation may in step S506 be regenerated based on vectors 104 to a larger number of the constituent parts of the marker 102. The regenerated representations may then be fed back to step S504.

In case the regenerated representations can still not be matched, or alternatively to step S506, in step S508 the representations may be matched based on a similarity score and in relation to a predetermined level of the similarity score. The similarity score may be a Kullback-Leibler divergence. Thus, the first and second representations may be matched based on their probabilistic similarity rather than the identity of the first and second representation.

The method described above may be applied to a plurality of hydrogel beads 100, with each bead 100 having a unique marker 102. In this case a first three-dimensional image and a second three-dimensional image for each of the hydrogel beads 100 is used to generate respective first and second representations. In addition, subsequent three-dimensional images of each of the hydrogel beads 100 may be used to generate further representations and match those to the first and second representations. The first, second and subsequent images may be generated by means of a microscope, in particular, a light sheet microscope.

As used herein the term "and/or" includes any and all combinations of one or more of the associated listed items and may be abbreviated as "/".

Although some aspects have been described in the context of an apparatus, it is clear that these aspects also represent a description of the corresponding method, where a block or device corresponds to a method step or a feature of a method step. Analogously, aspects described in the context of a method step also represent a description of a corresponding block or item or feature of a corresponding apparatus.

Figure 6:
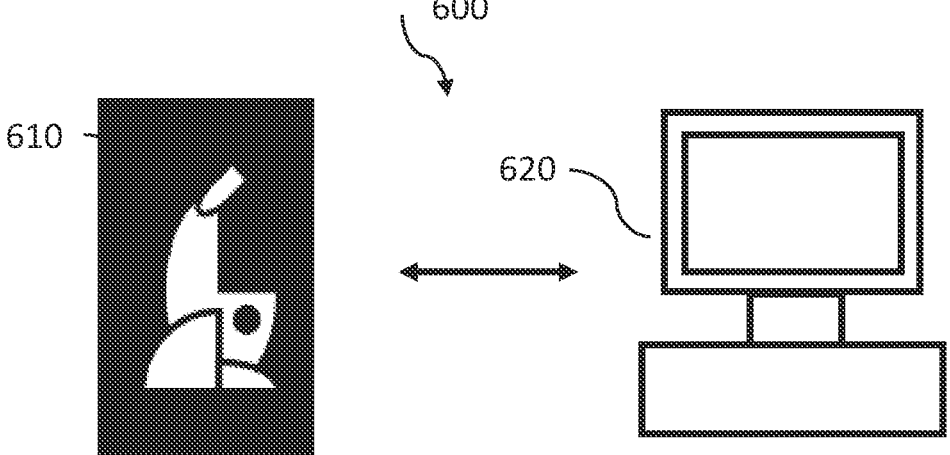
FIG. 6 shows a schematic illustration of a system configured to perform a method described herein.

Some embodiments relate to a microscope comprising a system as described in connection with one or more of the FIGS. 1 to 5. Alternatively, a microscope may be part of or connected to a system as described in connection with one or more of the FIGS. 1 to 5. FIG. 6 shows a schematic illustration of a system 600 configured to perform a method described herein. The system 600 comprises a microscope 610 and a computer system 620. The microscope 610 is configured to take images and is connected to the computer system 620. The computer system 620 is configured to execute at least a part of a method described herein. The computer system 620 may be configured to execute a machine learning algorithm. The computer system 620 and microscope 610 may be separate entities but can also be integrated together in one common housing. The computer system 620 may be part of a central processing system of the microscope 610 and/or the computer system 620 may be part of a subcomponent of the microscope 610, such as a sensor, an actor, a camera or an illumination unit, etc. of the microscope 610.

The computer system 620 may be a local computer device (e.g. personal computer, laptop, tablet computer or mobile phone) with one or more processors and one or more storage devices or may be a distributed computer system (e.g. a cloud computing system with one or more processors and one or more storage devices distributed at various locations, for example, at a local client and/or one or more remote server farms and/or data centers). The computer system 620 may comprise any circuit or combination of circuits. In one embodiment, the computer system 620 may include one or more processors which can be of any type. As used herein, processor may mean any type of computational circuit, such as but not limited to a microprocessor, a microcontroller, a complex instruction set computing (CISC) microprocessor, a reduced instruction set computing (RISC) microprocessor, a very long instruction word (VLIW) microprocessor, a graphics processor, a digital signal processor (DSP), multiple core processor, a field programmable gate array (FPGA), for example, of a microscope or a microscope component (e.g. camera) or any other type of processor or processing circuit. Other types of circuits that may be included in the computer system 620 may be a custom circuit, an application-specific integrated circuit (ASIC), or the like, such as, for example, one or more circuits (such as a communication circuit) for use in wireless devices like mobile tele-phones, tablet computers, laptop computers, two-way radios, and similar electronic systems. The computer system 620 may include one or more storage devices, which may include one or more memory elements suitable to the particular application, such as a main memory in the form of random access memory (RAM), one or more hard drives, and/or one or more drives that handle removable media such as compact disks (CD), flash memory cards, digital video disk (DVD), and the like. The computer system 620 may also include a display device, one or more speakers, and a keyboard and/or controller, which can include a mouse, trackball, touch screen, voice-recognition device, or any other device that permits a system user to input information into and receive information from the computer system 620.

Some or all of the method steps may be executed by (or using) a hardware apparatus, like for example, a processor, a microprocessor, a programmable computer or an electronic circuit. In some embodiments, some one or more of the most important method steps may be executed by such an apparatus.

Depending on certain implementation requirements, embodiments of the invention can be implemented in hardware or in software. The implementation can be performed using a non-transitory storage medium such as a digital storage medium, for example a floppy disc, a DVD, a Blu-Ray, a CD, a ROM, a PROM, and EPROM, an EEPROM or a FLASH memory, having electronically readable control signals stored thereon, which cooperate (or are capable of cooperating) with a programmable computer system such that the respective method is performed. Therefore, the digital storage medium may be computer readable.

Some embodiments according to the invention comprise a data carrier having electronically readable control signals, which are capable of cooperating with a programmable computer system, such that one of the methods described herein is performed.

Generally, embodiments of the present invention can be implemented as a computer program product with a program code, the program code being operative for performing one of the methods when the computer program product runs on a computer. The program code may, for example, be stored on a machine readable carrier.

Other embodiments comprise the computer program for performing one of the methods described herein, stored on a machine readable carrier.

In other words, an embodiment of the present invention is, therefore, a computer program having a program code for performing one of the methods described herein, when the computer program runs on a computer.

A further embodiment of the present invention is, therefore, a storage medium (or a data carrier, or a computer-readable medium) comprising, stored thereon, the computer program for performing one of the methods described herein when it is performed by a processor. The data carrier, the digital storage medium or the recorded medium are typically tangible and/or non-transitionary. A further embodiment of the present invention is an apparatus as described herein comprising a processor and the storage medium.

A further embodiment of the invention is, therefore, a data stream or a sequence of signals representing the computer program for performing one of the methods described herein. The data stream or the sequence of signals may, for example, be configured to be transferred via a data communication connection, for example, via the internet.

A further embodiment comprises a processing means, for example, a computer or a programmable logic device, configured to, or adapted to, perform one of the methods described herein.

A further embodiment comprises a computer having installed thereon the computer program for performing one of the methods described herein.

A further embodiment according to the invention comprises an apparatus or a system configured to transfer (for example, electronically or optically) a computer program for performing one of the methods described herein to a receiver. The receiver may, for example, be a computer, a mobile device, a memory device or the like. The apparatus or system may, for example, comprise a file server for transferring the computer program to the receiver.

In some embodiments, a programmable logic device (for example, a field programmable gate array) may be used to perform some or all of the functionalities of the methods described herein. In some embodiments, a field programmable gate array may cooperate with a microprocessor in order to perform one of the methods described herein. Generally, the methods are preferably performed by any hardware apparatus.

While subject matter of the present disclosure has been illustrated and described in detail in the drawings and foregoing description, such illustration and description are to be considered illustrative or exemplary and not restrictive. Any statement made herein characterizing the invention is also to be considered illustrative or exemplary and not restrictive as the invention is defined by the claims. It will be understood that changes and modifications may be made, by those of ordinary skill in the art, within the scope of the following claims, which may include any combination of features from different embodiments described above.

The terms used in the claims should be construed to have the broadest reasonable interpretation consistent with the foregoing description. For example, the use of the article "a" or "the" in introducing an element should not be interpreted as being exclusive of a plurality of elements. Likewise, the recitation of "or" should be interpreted as being inclusive, such that the recitation of "A or B" is not exclusive of "A and B," unless it is clear from the context or the foregoing description that only one of A and B is intended. Further, the recitation of "at least one of A, B and C" should be interpreted as one or more of a group of elements consisting of A, B and C, and should not be interpreted as requiring at least one of each of the listed elements A, B and C, regardless of whether A, B and C are related as categories or otherwise. Moreover, the recitation of "A, B and/or C" or "at least one of A, B or C" should be interpreted as including any singular entity from the listed elements, e.g., A, any subset from the listed elements, e.g., A and B, or the entire list of elements A, B and C.

LIST OF REFERENCE SIGNS

100 Discrete entity, hydrogel bead
102 Marker
103 Image
104 Vector
108 Biological sample
110 Microbead
112 Centre of mass of hydrogel bead
200, 302, 304, 306 Representation
300 Angle between vectors
400, 402, 404, 406 Histogram
408, 410, 412, 414 Hash value
416 Hash function
600 System
610 Microscope
620 Computer system

The invention claimed is:

1. A method for matching a three-dimensional first image of at least one discrete entity with at least a three-dimensional second image of the at least one discrete entity, the at least one discrete entity comprising a biological sample and a plurality of constituent parts of a marker, and the three-dimensional images are acquired by a microscope, the method comprising:
    generating a first representation of the marker from the three-dimensional first image;
    generating a second representation of the marker from the three-dimensional second image; and
    matching the three-dimensional first image with the three-dimensional second image by comparing the first representation and the second representation to recognize the at least one discrete entity in subsequent images acquired after the first image;
    wherein generating the first representation and the second representation comprises determining vectors from a position of at least one reference item in the respective three-dimensional image to at least a position of some of the plurality of constituent parts of the marker in the respective three-dimensional image, determining for the vectors at least one value of a property of the vectors, and generating the first representation or the second representation of the marker based on a frequency of the at least one value of the property, wherein the marker is an optically detectable structure, and wherein the at least one reference item is a center of mass of one of the constituent parts of the marker.

2. The method according to claim 1, wherein the property of the vectors is a length of the vectors or an angle between the vectors.

3. The method according to claim 1, wherein the first representation or second representation is generated as a hash value of the frequency of the values of the property.

4. The method according to claim 3, wherein the three-dimensional first image is matched with the three-dimensional second image based upon the hash value of the first representation and the hash value of the second representation being identical.

5. The method according to claim 1, wherein the frequency of the values of the property are determined with a histogram.

6. The method according to claim 1, further comprising rejecting the match between the three-dimensional first image and the three-dimensional second image based on the comparison, and wherein when rejecting the match, a similarity score is determined between the first representation and the second representation and the first representation and the second representation are matched in relation to a predetermined level of the similarity score.

7. The method according to claim 6, wherein the similarity score is determined based on a Kullback-Leibler divergence.

8. The method according to claim 1, further comprising rejecting the match between the three-dimensional first image and the three-dimensional second image based on the comparison, and wherein when rejecting the match, the first representation and the second representation are regenerated from the three-dimensional first image and the three-dimensional second image by determining the vectors from the at least one reference item to more than the at least some of the plurality of constituent parts of the marker when generating the first representation and the second representation.

9. The method according to claim 1, wherein the at least one reference item is at least one of: a center of mass of the discrete entity, or an optically detectable feature of the discrete entity.

10. The method according to claim 1, wherein the at least one discrete entity is comprised of a polymeric compound.

11. The method according to claim 1, wherein the plurality of constituent parts of the marker are microbeads, at least a partial surface of the at least one discrete entity, which is stained with at least one fluorescent dye, or an area of the least one discrete entity, which is stained with at least one fluorescent dye.

12. The method according to claim 1, wherein the three-dimensional first image or the three-dimensional second image is acquired by combining multiple, parallel images acquired throughout the at least one discrete entity.

13. The method according to claim 1, wherein the biological sample comprises at least one cell.

14. A non-transitory computer-readable medium having processor-executable instructions stored thereon, wherein the processor-executable instructions, when executed by the one or more processors, facilitate performance of the method according to claim 1.

15. A computation device comprising a memory storing a program code and at least one processor, the at least one processor being configured to execute the program code which, when executed by the at least one processor, causes the computation device to carry out the method according to claim 1.

16. The method according to claim 1, wherein the at least one discrete entity is a hydrogel bead, or wherein the at least one discrete entity is comprised of a polymeric compound including at least one of agarose, alginate, chitosan, hyaluronan, dextran, collagen and fibrin as well as poly(ethylene glycol), poly(hydroxyethyl methacrylate), poly(vinyl alcohol), and poly(caprolactone).

17. The method according to claim 1, wherein the frequency of the at least one value of the property are determined by generating a histogram from values of the property of the vector using a particular bin size.

18. An imaging device for matching a three-dimensional first image of at least one discrete entity with at least a three-dimensional second image of the at least one discrete entity, the discrete entity comprising a biological sample and a plurality of constituent parts of a marker, and the three-dimensional images are acquired by a microscope, the device comprising:

an imaging container to contain the at least one discrete entity;

a detector and optical means for imaging at least partially the at least one discrete entity onto the detector; and a control unit configured to:

acquire the three-dimensional first image of the at least one discrete entity;

generate a first representation of the marker from the three-dimensional first image;

acquire the three-dimensional second image of the at least one discrete entity;

generate a second representation of the marker from the three-dimensional second image; and match the three-dimensional first image with the three-dimensional second image by comparing the first representation and the second representation to recognize the at least one discrete entity in subsequent images acquired after the first image, wherein generating the first representation and the second representation comprises determining vectors from a position of at least one reference item in the respective three-dimensional image to at least a position of some of the plurality of constituent parts of the marker in the respective three-dimensional image, determining for the vectors at least one value of a property of the vectors, and generating the representation of the marker based on a frequency of the at least one value of the property, wherein the marker is an optically detectable structure, and wherein the at least one reference item is a center of mass of one of the constituent parts of the marker.

\* \* \* \* \*